(12) United States Patent
Ishikawa et al.

(10) Patent No.: US 7,492,942 B2
(45) Date of Patent: *Feb. 17, 2009

(54) IMAGE DEFECT INSPECTION METHOD, IMAGE DEFECT INSPECTION APPARATUS, AND APPEARANCE INSPECTION APPARATUS

(75) Inventors: Akio Ishikawa, Hachioji (JP); Shinji Ueyama, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 253 days.

This patent is subject to a terminal disclaimer.

(21) Appl. No.: 11/206,706

(22) Filed: Aug. 17, 2005

(65) Prior Publication Data

US 2006/0098863 A1 May 11, 2006
US 2008/0260236 A9 Oct. 23, 2008

(30) Foreign Application Priority Data

Nov. 11, 2004 (JP) ............................. 2004-327759

(51) Int. Cl.
 *G06K 9/00* (2006.01)
(52) U.S. Cl. ...................... 382/145; 382/149; 382/168; 382/169; 382/172
(58) Field of Classification Search ................ 382/145, 382/149, 168, 169, 172
See application file for complete search history.

(56) References Cited

U.S. PATENT DOCUMENTS 6,137,541 A * 10/2000 Murayama .................. 348/673

2004/0062432 A1 4/2004 Ishikawa

FOREIGN PATENT DOCUMENTS

| JP | 4-107946 | 4/1992 |
|----|----------|--------|
| JP | 2996263 | 10/1999 |
| JP | 2002-22421 | 1/2002 |
| JP | 2004-177397 | 6/2004 |

OTHER PUBLICATIONS

Machine translation of JP 2004-177397.*
Patent Abstract of Japan, Publication No. 04107946 A, Published on Apr. 9, 1992, in the name of Taniguchi, et al.
Patent Abstract of Japan, Publication No. 05047886 A, Corresponding to JP 2996263, Published on Feb. 26, 1993, in the name of Jingu.
Patent Abstract of Japan, Publication No. 2002022421 A, Published on Jan. 23, 2002, in the name of Hikita, et al.
Patent Abstract of Japan, Publication No. 2004177397 A, Published on Jun. 24, 2004, in the name of Ishikawa.

* cited by examiner

*Primary Examiner*—John B Strege
(74) *Attorney, Agent, or Firm*—Christie, Parker & Hale, LLP

(57) ABSTRACT

In an image defect inspection method and apparatus, which detects a gray level difference between the corresponding portions of two images, automatically sets a threshold value based on the distribution of the detected gray level difference, compares the detected gray level difference with the threshold value, and judges one or the other of the portions to be defective if the gray level difference is larger than the threshold value, provisions are made to reduce the occurrence of false defects when there is a brightness difference between the two images undergoing the comparison. In the image defect inspection method, the brightness difference between the two images is computed (S106), and the threshold value is determined in such a manner that the threshold value increases with the computed brightness difference (S107).

10 Claims, 16 Drawing Sheets

IMAGE DEFECT INSPECTION METHOD, IMAGE DEFECT INSPECTION APPARATUS, AND APPEARANCE INSPECTION APPARATUS

CROSS-REFERENCE TO RELATED APPLICATION

This application is claims priority of Japanese Patent Application Number 2004-327759, filed on Nov. 11, 2004.

BACKGROUND OF THE INVENTION

1. Field of the Invention

The present invention relates to a defect inspection method and apparatus which detects a difference between corresponding signals, compares the detected difference with a threshold value, and judges the part under examination to be defective if the difference is larger than the threshold value. More particularly, the invention relates to an image defect inspection method and apparatus which detects a gray level difference between corresponding portions of two images, compares the detected gray level difference with a threshold value, and judges one or the other of the portions to be defective if the gray level difference is larger than the threshold value, and also relates to an appearance inspection apparatus which, by using such a method, detects a defect in a semiconductor circuit pattern formed on a semiconductor wafer. Still more particularly, the present invention relates to a technique for determining such a threshold value in accordance with the above signals (images).

2. Description of the Related Art

The present invention is directed to an image processing method and apparatus which compares corresponding portions between two images that should be the same, and judges any portion where the difference is large to be defective. The description herein is given by taking as an example an appearance inspection apparatus (inspection machine) for detecting a defect in a semiconductor circuit pattern formed on a semiconductor wafer during a semiconductor manufacturing process, but the invention is not limited to this particular type of apparatus. Generally, a bright field inspection apparatus, in which the surface of a sample is illuminated from a vertical direction and the image of its reflected light is captured, is employed for such an appearance inspection apparatus, but a dark field inspection apparatus which does not directly capture the illumination light is also used. In the case of the dark field inspection apparatus, the surface of the sample is illuminated from an oblique or a vertical direction, and a sensor is disposed so as not to detect specularly reflected light. Then, the dark field image of the surface of the sample is obtained by sequentially scanning the surface with the illumination light. Accordingly, some dark field apparatuses may not use an image sensor, but it will be appreciated the present invention is also applicable to such apparatuses. In this way, the present invention is applicable to any image processing method and apparatus as long as the method and apparatus are designed to compare corresponding portions between two images (signals) that should be the same, and to judge any portion where the difference is large to be defective.

In a semiconductor manufacturing process, many chips (dies) are formed on a semiconductor wafer. Patterns are formed in multiple layers on each die. Each completed die is electrically tested using a prober and a tester, and any defective die is removed from the assembly process. In a semiconductor manufacturing process, the manufacturing yield is a very important factor, and the result of the electrical testing is fed back to the manufacturing process and used for the management of each process step. However, as the semiconductor manufacturing process consists of many process steps, it takes a very long time before the electrical testing can be conducted after the manufacturing is started. Therefore, when, for example, a certain process step is found faulty as a result of the electrical testing, many wafers are already partway through the process and, thus, the result of the electrical testing cannot be easily utilized to improve the yield. In view of this, pattern defect inspection is performed to inspect formed patterns in the middle of the process in order to detect pattern defects. If the pattern defect inspection is performed at a plurality of steps in the manufacturing process, it becomes possible to detect defects that occurred after the preceding inspection, and the result of the inspection can thus be promptly reflected in the process management.

In an appearance inspection apparatus currently in use, a semiconductor wafer is illuminated, an image of a semiconductor circuit pattern is optically captured, and an electrical image signal is generated which is further converted into a multi-valued digital signal (digital gray level signal). Then, a difference signal (gray level difference signal) is generated that represents the difference between the gray level signal of the pattern under inspection and the gray level signal of a reference pattern, and any portion where the difference is larger than a predetermined threshold value is judged to be defective.

Generally, the reference pattern is a neighboring die or a neighboring similar pattern. Then, a defect grouping process is performed in which the portion that has been judged to be defective is examined in further detail to determine whether the defect is a true defect that affects the yield. The defect grouping process takes a long time because each defective portion needs to be examined in detail. Therefore, in the defect judgment, it is required that any true defect be invariably judged to be a defect, while minimizing the possibility of judging any defect other than a true defect to be a defect.

To achieve this, an optimum setting of the threshold value is critical. If the threshold value is set too small, the number of pixels judged to be defective will increase, and portions not truly defective will be judged defective, thus resulting in the problem that the time required for the defect grouping process increases. Conversely, if the threshold value is set too large, even true defects may be judged not to be defects, resulting in the problem that the inspection is inadequate.

In a prior art method that automatically determines the threshold value according to each sample, the digital gray level signal of the pattern of a similar sample is generated in advance, followed by the generation of a gray level difference signal, and a histogram of gray level differences is created. Then, a variation reference difference, which is set by a prescribed proportion of a portion where the gray level difference is large in the histogram, is obtained, and the threshold value for detection is determined by adding a fixed difference to the reference difference. The reason for this is to prevent the number of pixels judged to be defective from increasing appreciably in cases where the variance of the distribution of the differences is large, by considering that such cases can become a problem in practice. In this method, the variation reference difference varies from sample to sample, but the fixed difference to be added is fixed and does not vary from sample to sample; accordingly, this method has the problem that the proper threshold value cannot be determined when the noise level varies.

To solve the above problem, various methods for determining the threshold value have been proposed. For example, Japanese Unexamined Patent Publication No. H04-107946 discloses a method that determines the threshold value based on the statistics of gray level differences computed at a plurality of portions of a pattern. More specifically, a histogram of maximum values is created by obtaining the maximum value of the gray level difference for each portion. Then, based on the mean and the standard deviation of the gray level difference, the initial value of the optimum threshold value is set, and the optimum threshold value is determined by correcting the initial value based on the number of pixels detected as defective. This method, however, has the following problems: (1) samples must be measured in advance and (2) inspection must be performed a plurality of times. Furthermore, while it is stated that the threshold value at which the number of detected defects suddenly changes is optimum, no description is provided of a specific method for obtaining such a threshold value.

On the other hand, Japanese Patent No. 2996263 discloses a method in which an approximate curve is obtained from the relationship between the gray level difference and its frequency and the gray level difference at which the approximate curve becomes zero is taken as the optimum threshold value. Here, the relationship between the gray level difference and the frequency is represented by a curve, but a curve does not necessarily become zero; therefore, there are cases where the approximate curve does not become zero. Further, even in the case of a straight line, the straight line may not become zero, depending on its slope. Therefore, there can occur cases where the threshold value cannot be set. Furthermore, it is stated that the above curve can be obtained easily, but in actuality, this curve cannot be obtained easily because it depends on the distribution of gray level differences, and hence there arises the problem that the processing time increases.

Japanese Unexamined Patent Publication No. 2002-22421 discloses a method that performs a conversion to an error probability value by using a standard deviation. This method, however, involves the following problems: (1) as the standard deviation is computed directly from the gray level differences, a large amount of computation is required and the processing time increases, and (2) as the error probability value, not the gray level difference, is used to judge the presence or absence of a defect, the error probability value must be computed for every gray level difference, and this again increases the processing time. There is the further problem that, because of the use of the standard deviation, the method is only applicable to normal distributions and cannot be applied to other types of distribution.

For the inspection of semiconductor patterns, etc., it is desired to automate the inspection process, and it is also desired to automatically set the threshold value. To achieve this, there is a need to set the optimum threshold value by instantaneously processing the detected gray level differences and to judge the presence or absence of a defect based on the threshold value; one possible solution here would be to automatically set the threshold value by automatically performing a method such as described above. On the other hand, there is also a need to shorten the inspection time in order to improve throughput, but the above-described methods have problems such as the need to measure the samples a plurality of times in advance, the long processing time, etc. and, therefore, they are not suitable for automating the threshold value setting process in a high-throughout inspection apparatus.

In particular, in the inspection of an actual semiconductor pattern, the noise level differs depending not only on the portion within a die but also on the position of the die on the wafer; furthermore, even when the same semiconductor pattern is formed, the noise level differs from one wafer to another. Accordingly, there is a need to set the optimum threshold value by processing the gray level difference as it is detected, but none of the above-described prior art methods can satisfy such a need.

In view of the above background, the applicant of this patent application proposed the following image defect inspection method in Japanese Unexamined Patent Publication No. 2004-177397. That is, the distribution (histogram) of the gray level difference between corresponding portions of two images is created (see FIG. 1A), and its cumulative frequency is computed (see FIG. 1B). Then, assuming that the gray level difference has a distribution that obeys a prescribed type of distribution, a converted cumulative frequency is computed by converting the cumulative frequency so that the cumulative frequency shows a linear relationship to the gray level difference (see FIG. 1C). After that, an approximate straight line is computed by approximating the converted cumulative frequency by a straight line and, based on the computed approximate straight line, the threshold value is determined from a prescribed cumulative frequency value in accordance with a prescribed calculation method.

For example, in the example of FIG. 1C, the threshold value T is calculated as T=(P1−b+VOP)/a+HO, where "a" is the slope of the approximate straight line, "b" is the intercept at which the approximate straight line intersects the vertical axis, P1 is the cumulative frequency corresponding to the prescribed cumulative probability (p), and VOP and HO are prescribed sensitivity setting parameters.

As the converted cumulative frequency computed with this method shows a linear relationship to the gray level difference, subsequent processing for determining the threshold value is facilitated. As a result, the threshold value can be set automatically in a short time.

SUMMARY OF THE INVENTION

In the example shown in FIGS. 1A to 1C, the converted cumulative frequency is computed by assuming that the distribution of the gray levels of the two images to be compared is centered on the same value, that is, pixels with zero gray level differences occur most often.

In reality, however, such an assumption does not always holds true, and there can occur a case where the center of the distribution of the gray level differences is shifted from zero due to brightness differences (called "color unevenness") between the captured images of dies at various positions on the wafer.

If a defect inspection is performed using two images having appreciable color unevenness, false defects tend to occur because, on the average, the gray level difference becomes higher than would be the case if images with less color unevenness were used. Therefore, in the above cited Japanese Unexamined Patent Publication No. 2004-177397, the average of the gray level differences between two images or the gray level difference at which the cumulative frequency of the gray level difference is 50% is used, or two threshold values, one negative and the other positive, are calculated separately and the average value is obtained as a correction value, and the gray level difference between the two images is corrected so that pixels with zero differences occur most often.

However, when there is color unevenness in the gray level signals of the two images as described above, the spreading of the distribution of the gray level differences becomes wider compared with the case where there is no color unevenness. As a result, if the gray level difference signal between the two images is corrected as described above, the gray level difference signal is examined with high sensitivity, the resulting problem being that false defects can still occur.

In view of the above problem, it is an object of the present invention to provide an image defect inspection method and apparatus which detects a gray level difference between corresponding portions of two images, automatically sets a threshold value based on the distribution of the detected gray level difference, compares the detected gray level difference with the threshold value, and judges one or the other of the portions to be defective if the gray level difference is larger than the threshold value, wherein provisions are made to reduce the occurrence of false defects when there is a brightness difference between the two images undergoing the comparison.

To achieve the above object, in the image defect inspection method and the image defect inspection apparatus according to the present invention, the brightness difference between the two images under comparison is computed, and the threshold value is set in such a manner that the threshold value increases with the brightness difference.

The computation of the brightness difference is accomplished in the following manner. First, a positive- or negative-signed gray level difference is detected between the corresponding portions of the two images, and the cumulative frequency of the thus detected signed gray level difference is computed; then, the brightness difference is computed in relation to a signed gray level difference having a prescribed frequency in the thus computed cumulative frequency of the detected signed gray level difference.

Alternatively, the computation of the brightness difference may be accomplished in the following manner. That is, the cumulative frequency of the signed gray level difference, computed as described above, is converted so as to yield a converted cumulative frequency such that the cumulative frequency shows a linear relationship to the signed gray level difference when the signed gray level difference is assumed to have a distribution that obeys a prescribed type of distribution, and an approximate straight line is computed by approximating the converted cumulative frequency by a straight line; then, the brightness difference is computed in relation to a signed gray level difference having a prescribed frequency in the approximate straight line.

The prescribed type of distribution can be any type of distribution; for example, the distribution is one selected from the group consisting of a normal distribution, a Poisson distribution, a t-distribution, an exponential distribution, a Weibull distribution, and a chi-squared distribution.

Further alternatively, a gray level difference at which the distribution of the detected signed gray level difference peaks may be obtained directly, and the brightness difference may be computed in relation to that gray level difference.

The threshold value may be determined in the form of an absolute threshold value with which an unsigned absolute gray level difference signal is to be compared, or in the form of positive and negative two threshold values with which singed gray level difference signals are to be compared.

The absolute threshold value is determined in the following manner. The positive- or negative-signed gray level difference is detected between the corresponding portions of the two images, an unsigned absolute gray level difference is computed from the signed gray level difference, the cumulative frequency of the absolute gray level difference is computed, and the converted cumulative frequency is computed by converting the cumulative frequency so that the cumulative frequency shows a linear relationship to the absolute gray level difference when the absolute gray level difference is assumed to have a distribution that obeys a prescribed type of distribution; then, the approximate straight line is computed by approximating the converted cumulative frequency by a straight line, and the absolute threshold value is determined by applying the approximate straight line, a prescribed cumulative frequency value, and the brightness difference to a prescribed calculation method.

Then, the defect inspection is performed by comparing the absolute gray level difference with the thus determined absolute threshold value.

Alternatively, the average value of the signed gray level difference is computed so that the distribution of the signed gray level difference used in the defect inspection is centered on the gray level difference of zero, and the signed gray level difference is corrected by the average value to compute a positive- or negative signed corrected gray level difference, from which an unsigned corrected absolute gray level difference is further computed; then, a corrected absolute threshold value is determined based on the corrected absolute gray level difference, and the defect inspection is performed by comparing the corrected absolute gray level difference with the corrected absolute threshold value.

The two, positive and negative, threshold values are determined in the following manner. First, the positive- or negative-signed gray level difference is detected, the cumulative frequency of the signed gray level difference is computed, and the converted cumulative frequency is computed by converting the cumulative frequency so that the cumulative frequency shows a linear relationship to the signed gray level difference when the signed gray level difference is assumed to have a distribution that obeys a prescribed type of distribution; then the approximate straight line is computed by approximating the converted cumulative frequency by a straight line, and the positive and negative two threshold values are determined by applying the approximate straight line, a prescribed cumulative frequency value, and the brightness difference to a prescribed calculation method.

When the threshold value is determined in the form of the positive and negative two threshold values, the brightness difference may be computed by using either the distribution of the signed gray level difference or the cumulative frequency or the approximate straight line computed when determining the two threshold values.

Alternatively, after computing the two, positive and negative, threshold values as described above, a value representing one half of the difference between the two values may be determined as the corrected threshold value; in that case, the corrected absolute gray level difference is computed by correcting the signed gray level difference by the mean of the positive and negative two threshold values, and the defect inspection is performed by comparing the corrected absolute gray level difference with the corrected threshold value.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Preferred embodiments of the present invention will be described in detail below while referring to the attached drawings.

Figure 2:
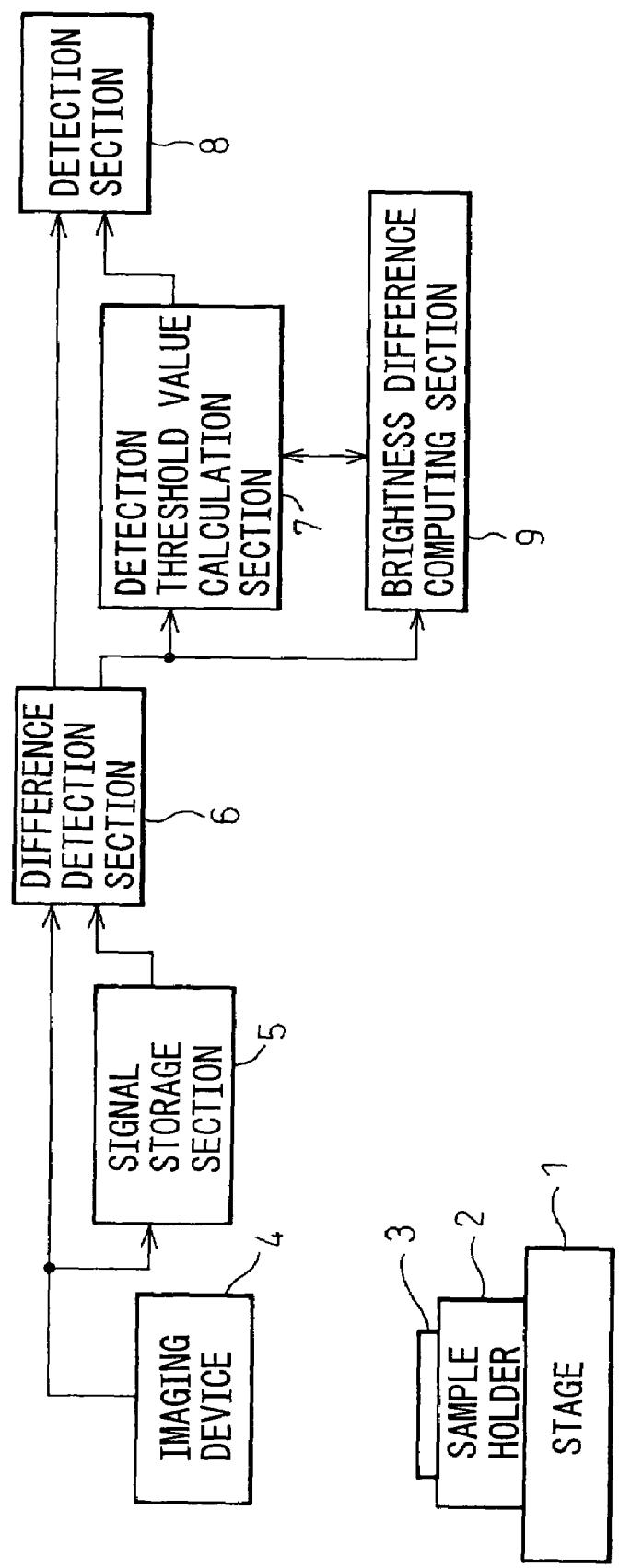
FIG. 2 is a block diagram showing the general configuration of an appearance inspection apparatus according to a first embodiment of the present invention.

FIG. 2 is a block diagram showing the general configuration of a semiconductor pattern appearance inspection apparatus according to a first embodiment of the present invention. As shown, a sample holder (chuck stage) 2 is mounted on the upper surface of a stage 1 which is freely movable in two- or three-dimensional directions. A semiconductor wafer 3 to be inspected is placed and fixed onto the sample holder. An imaging device 4 comprising a one-dimensional or two-dimensional CCD camera or the like is disposed above the stage, and the imaging device 4 produces an image signal by capturing an image of a pattern formed on the semiconductor wafer 3.

Figure 3:
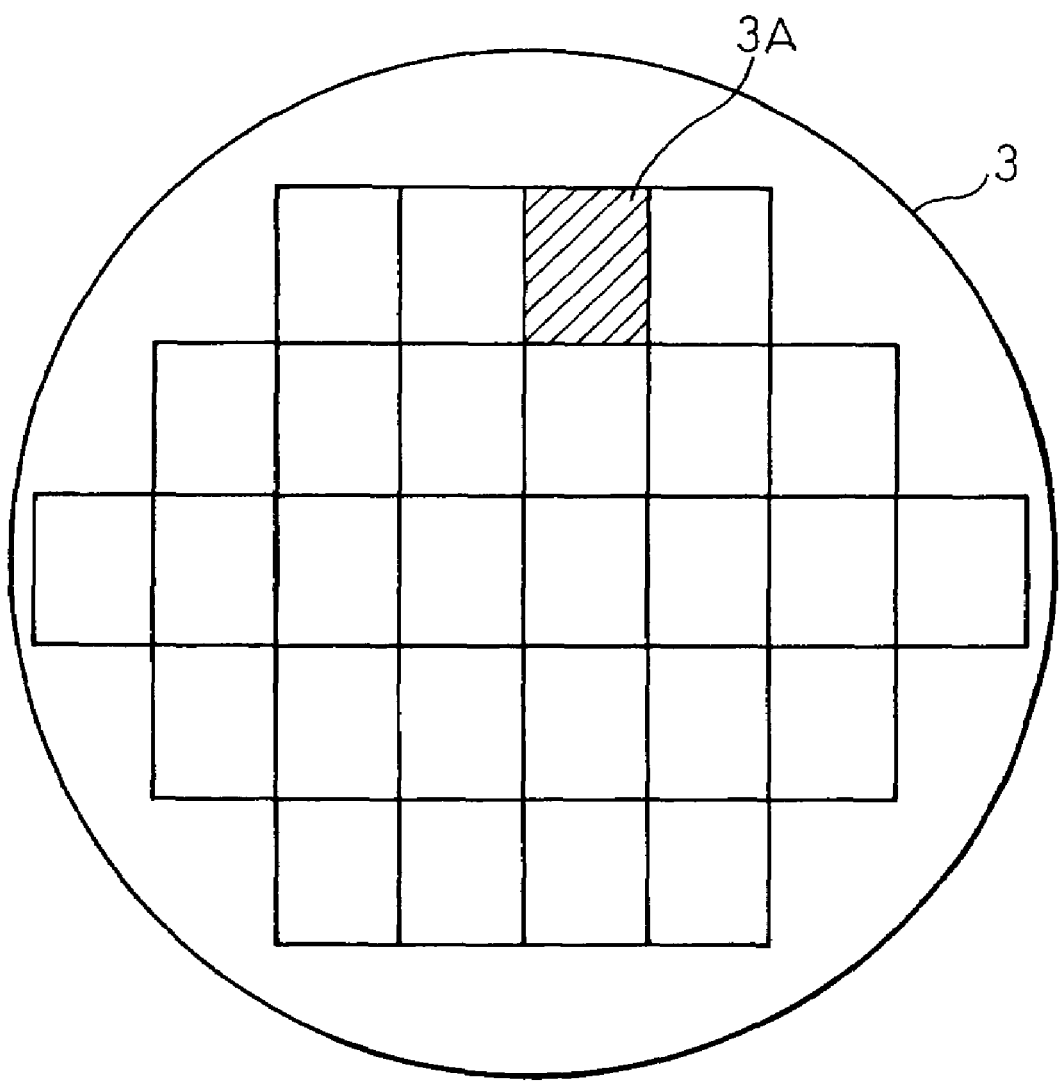
FIG. 3 is a diagram showing an arrangement of dies on a semiconductor wafer.

As shown in FIG. 3, a plurality of dies 3A are formed on the semiconductor wafer 3 in a matrix pattern repeating in X and Y directions. As the same pattern is formed on each die, it is general practice to compare the images of corresponding portions between adjacent dies. If there is no defect in any of the two adjacent dies, the gray level difference between them is smaller than a threshold value, but if there is a defect in either one of the dies, the gray level difference is larger than the threshold value (single detection). At this stage, however, this is no way to know which die contains the defect; therefore, the die is further compared with another die adjacent on a different side and, if the gray level difference in the same portion is larger than the threshold value, then it is determined that the die is defective (double detection).

The imaging device 4 is constructed from a one-dimensional CCD camera, and the stage 1 moves so that the imaging device 4 moves (scans) at a constant speed in the X or Y direction relative to the semiconductor wafer 3. The image signal is converted into a multi-valued digital signal (gray level signal) which is supplied to a difference detection section 6 and also to a signal storage section 5 for storing therein. As the scanning proceeds, a gray level signal is generated from the adjacent die, in synchronism with which the gray level signal of the preceding die is read out of the signal storage section 5 and supplied to the difference detection section 6. Actually, processing such as fine registration is also performed, but a detailed description of such processing will not be given here.

In this way, the gray level signals of the two adjacent die images are input to the difference detection section 6 where the difference (gray level difference) between the two gray level signals is computed, which is then supplied to a detection threshold value calculation section 7, a detection section 8, and a brightness difference computing section 9. Here, the difference detection section 6 computes the gray level difference (with a positive or negative sign) and outputs it as the gray level difference.

From the gray level difference, the brightness difference computing section 9 computes the brightness difference (color unevenness) between the two die images. The detection threshold value calculation section 7 determines the detection threshold value based on the gray level difference and the color unevenness thus computed, and supplies the threshold value to the detection section 8. The detection section 8 compares the gray level difference with the thus determined threshold value to determine whether there exists a defect. Generally, the noise level of a semiconductor pattern differs depending on the kind of the pattern such as the pattern of a memory cell portion, the pattern of a logic circuit portion, the pattern of a wiring portion, or the pattern of an analog circuit portion. Correspondence between each portion and the kind of the semiconductor pattern can be found from the design data. Therefore, for example, the detection threshold value calculation section 7 determines the threshold value by performing threshold value determining processing for each portion, and the detection section 8 makes a decision by using the threshold value determined for each portion.

In the present embodiment, the signal storage section 5 is provided in order to compare the images of adjacent dies on the semiconductor wafer, but the gray level difference can also be generated by supplying, to the difference detection section 6, the image signal of a reference sample separately stored or an image signal generated from data such as CAD; in that case, the signal storage section 5 can be eliminated.

The general configuration of the appearance inspection apparatus of the first embodiment has been described above, but the feature of the present invention lies in the provision of the detection threshold value calculation section 7 and the brightness difference computing section 9, the general configuration of which will be described with reference to the block diagram of FIG. 4.

Figure 4:
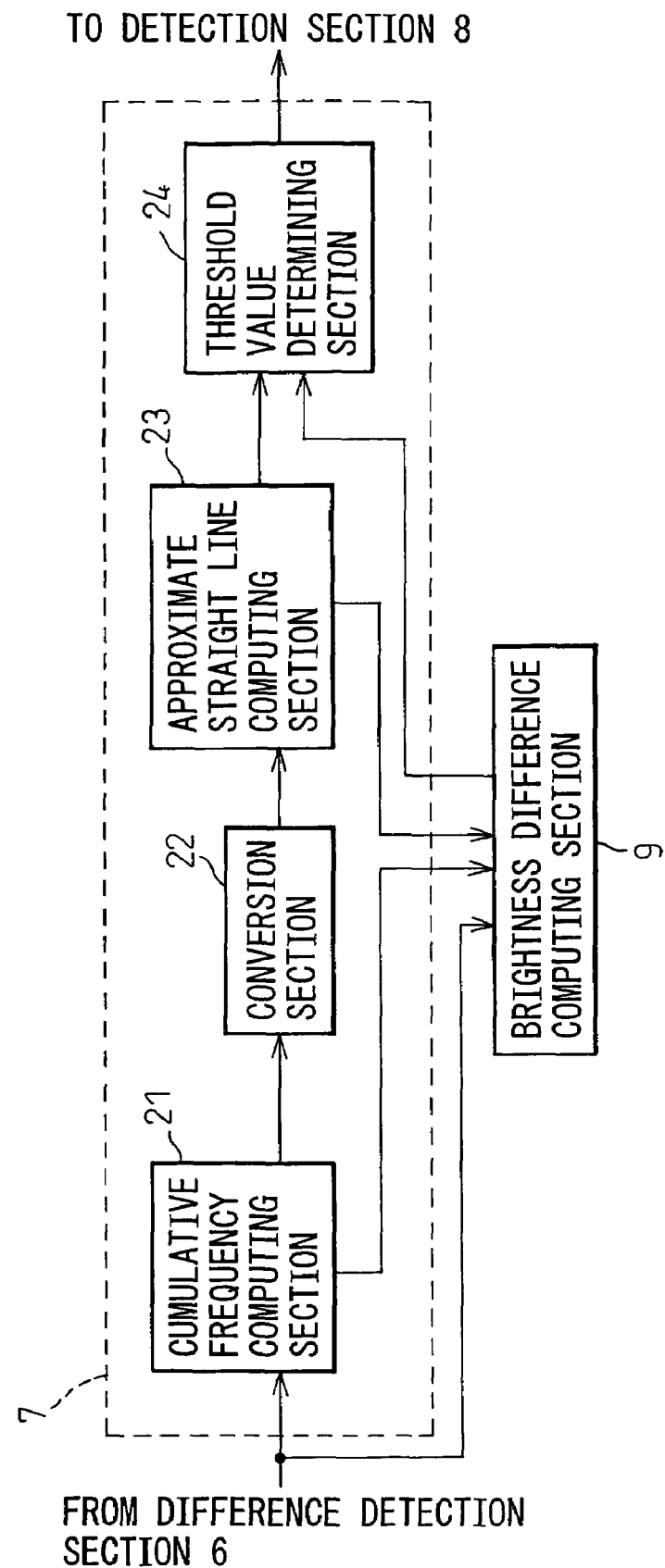
FIG. 4 is a block diagram showing the general configuration of a detection threshold value calculation section along with a brightness difference computing section in the appearance inspection apparatus of FIG. 2.

FIG. 4 is a block diagram showing the general configuration of the detection threshold value calculation section 7 along with the brightness difference computing section 9.

As shown, the detection threshold value calculation section 7 comprises: a cumulative frequency computing section 21 which takes as an input the positive- or negative-signed gray level difference supplied from the difference detection section 6, and computes its cumulative frequency; a conversion section 22 which takes the cumulative frequency as an input, and computes a converted cumulative frequency by converting the cumulative frequency so that the cumulative frequency shows a linear relationship to the gray level difference; an approximate straight line computing section 23 which computes an approximate straight line by approximating the converted cumulative frequency by a straight line; and a threshold value determining section 24 which determines the detection threshold value by applying the approximate straight line, the brightness difference computed by the brightness difference computing section 9, and a prescribed cumulative frequency value to a prescribed calculation method.

The brightness difference computing section 9 computes the brightness difference between the two images under comparison, based on the gray level difference supplied from the difference detection section 6, the gray level difference cumulative frequency output from the cumulative frequency computing section 21, or the approximate straight line output from the approximate straight line computing section 23, and supplies the brightness difference to the threshold value determining section 24.

The operation of the thus configured detection threshold value calculation section 7 and the brightness difference computing section 9 will be described with reference to FIG. 1 and FIGS. 5 to 9.

Figure 5:
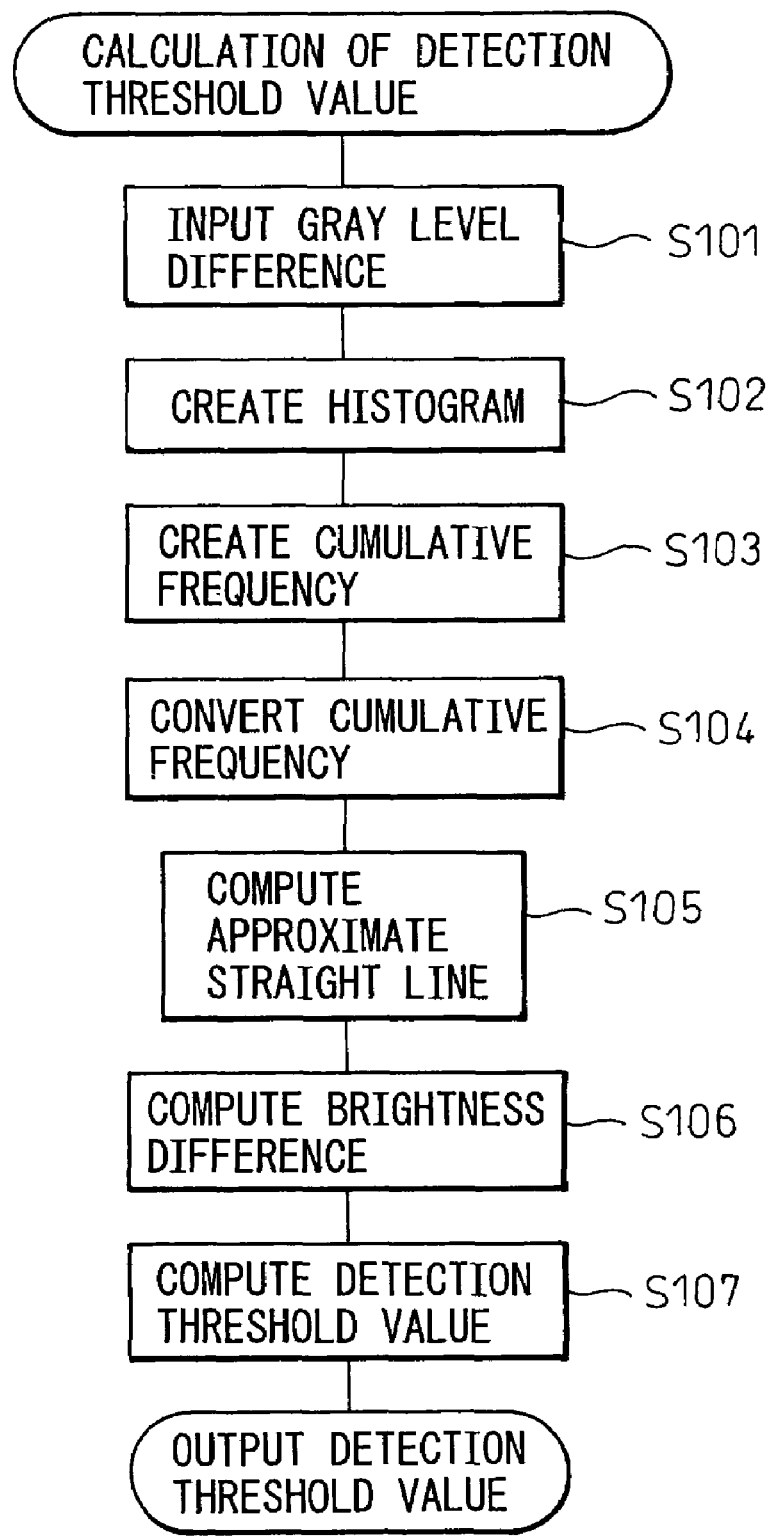
FIG. 5 is a basic flowchart illustrating a method of determining a detection threshold value according to the embodiment of the present invention.

FIG. 5 is a flowchart illustrating the basic operation of the detection threshold value calculation process according to the present invention. For examples of the graphs to be created in the process shown in the flowchart, reference should be made to the previously described FIGS. 1A to 1C.

Figure 1A:
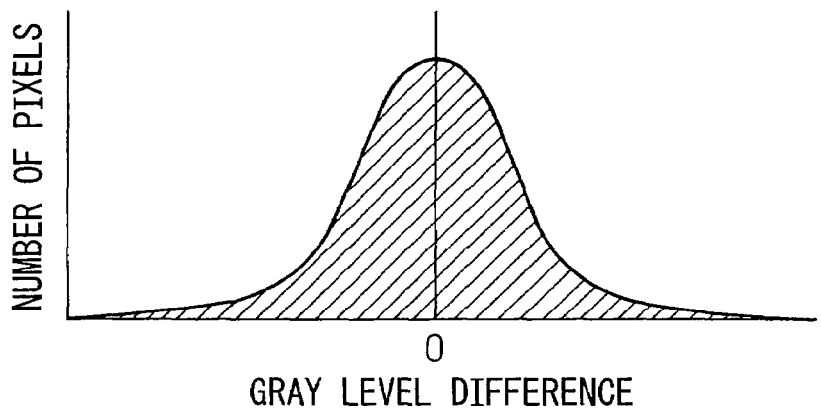
FIGS. 1A to 1C are diagrams for explaining a prior art image defect inspection method.
Figure 1B:
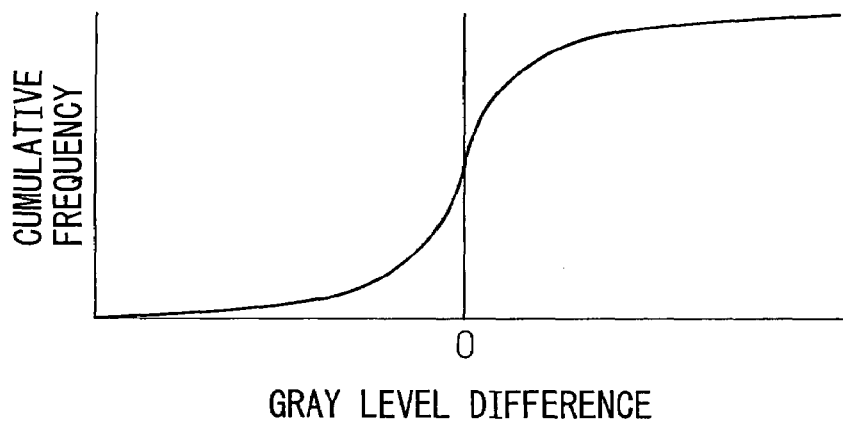
Figure 1C:
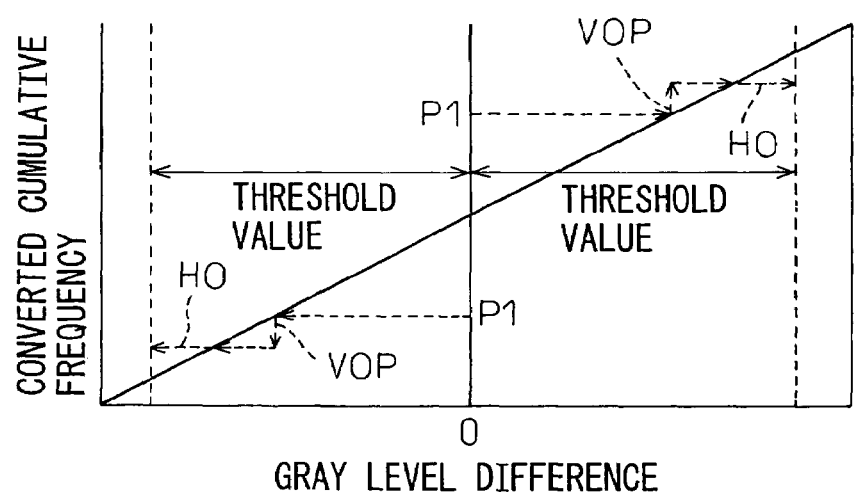

In step S101, the signed gray level difference calculated pixel by pixel by the difference detection section 6 is input to the cumulative frequency computing section 21. In step S102, the cumulative frequency computing section 21 creates a histogram of gray level differences such as shown in FIG. 1A. Here, if the number of pixels to be inspected is large, the histogram need not necessarily be created by using the gray level differences of all the pixels, but may be created by using the gray level differences only of selectively sampled pixels.

In step S103, the cumulative frequency computing section 21 creates the cumulative frequency of the gray level difference based on the histogram. Here, instead of the cumulative frequency, cumulative probability may be created, as will be described later. The cumulative frequency computing section 21 supplies the thus created cumulative frequency to the conversion section 22.

In step S104, assuming that the gray level difference obeys a certain type of distribution such as a normal distribution, a Poisson distribution, or a chi-squared distribution, the conversion section 22 converts the cumulative frequency so that the cumulative frequency shows a linear relationship to the gray level difference in the assumed distribution.

Figure 6A:
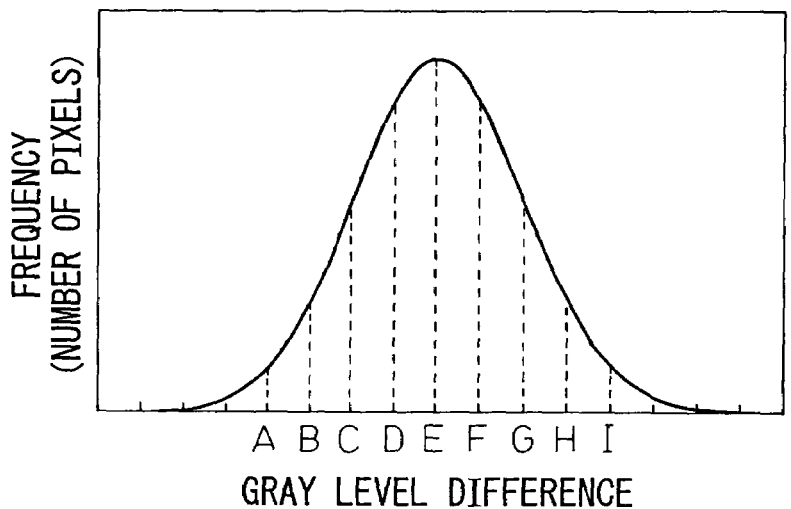
FIGS. 6A to 6C are diagrams for explaining the process for computing the converted cumulative frequency of a signed gray level difference.
Figure 6B:
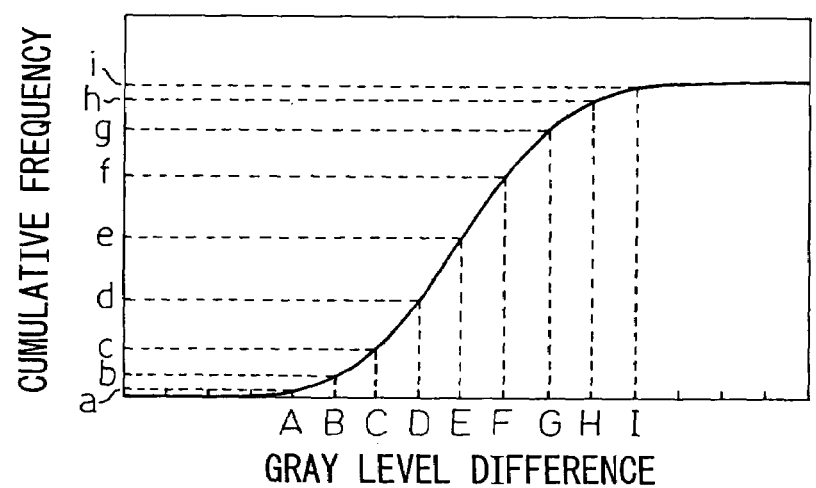

It is assumed that the frequency of the gray level difference has a certain distribution such as shown in FIG. 6A. Then, its cumulative frequency is a monotonically increasing curve such as shown in FIG. 6B. If the curve is represented by probabilities by dividing each cumulative frequency by the total number of samples, curves having the same coefficient, which shows how widespread the distribution is, are identical. Next, the cumulative frequency is converted so that the cumulative frequency shows a linear relationship to the gray level difference. To describe more specifically, if values "a" to "i" in FIG. 6B are converted so that they are proportional to values A to I, the graph shown in FIG. 6C results; here, if the values A to I are equally spaced apart, then the values "a" to "i" are also equally spaced apart. The cumulative frequency thus converted will be called the converted cumulative frequency. To describe this process more specifically, if the probability of the gray level difference is denoted by f(t), the cumulative probability F(t) (cumulative frequency/number of samples) is expressed by the following equation 1.

$$F(t) = \int_{-\infty}^{t} f(x)\,dx \quad (1)$$

Figure 6C:
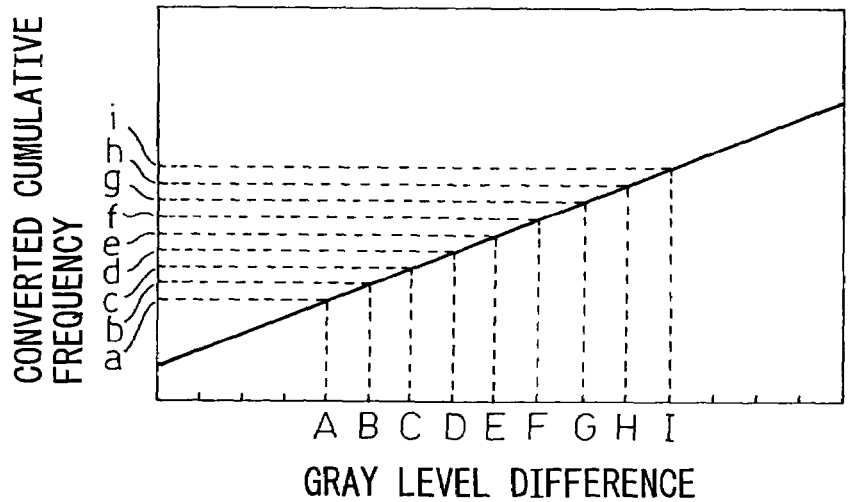

The conversion is accomplished by converting the cumulative probability by using the inverse function $F^{-1}(t)$ of the cumulative probability F(t). The converted cumulative frequency thus obtained is represented by a graph close to a straight line, such as shown in FIG. 6C. In the figure, the graph is shown in terms of cumulative frequency, but the graph is the same if it is shown in terms of cumulative probability. The converted cumulative frequency thus obtained is supplied to the approximate straight line computing section 23 at a subsequent stage.

As the computation for obtaining the inverse function of the cumulative probability requires a large amount of computation, the conversion is performed using a conversion table constructed in advance in accordance with the distribution. Further, the conversion need not be performed on all the cumulative frequency points, but need only be performed on the points necessary to obtain the approximate straight line hereinafter described. The assumed distribution can be created in advance by using a reference sample or a portion of the sample. When creating the assumed distribution from the reference, a histogram of gray level differences is created covering a region sufficiently larger than the range used to obtain the threshold value in the inspection. At this time, dies free from imperfections such as color unevenness are selected or an area containing such dies is selected or, as will be described later, the average value of the signed gray level differences is obtained and a correction is made so that the gray level difference becomes zero at the average value, or a correction is made so that the gray level difference becomes zero when the probability is 50%. Then, the conversion table is constructed by obtaining the cumulative probability for each of the equally spaced gray level differences.

In step S105, the approximate straight line computing section 23 computes the approximate straight line (y=ax+b) from the relationship between the gray level difference and the converted cumulative frequency. Here, the approximate straight line computing section 23 may compute approximate straight lines ($y=a_{(+)}x+b_{(+)}$ and $y=a_{(-)}x+b_{(-)}$) in the positive and negative gray level difference regions, respectively.

The approximate straight line can be obtained using a least squares method or the like but, more simply, the approximate straight line can be obtained by joining a certain point on the converted cumulative frequency to the origin by a straight line. Each computed approximate straight line is supplied to the threshold value determining section 24.

In step S106, the brightness difference computing section 9 computes the brightness difference between the two images under comparison, based on the signed gray level difference supplied from the difference detection section 6, the gray level difference cumulative frequency output from the cumulative frequency computing section 21, or the approximate straight line output from the approximate straight line computing section 23.

Figure 7A:
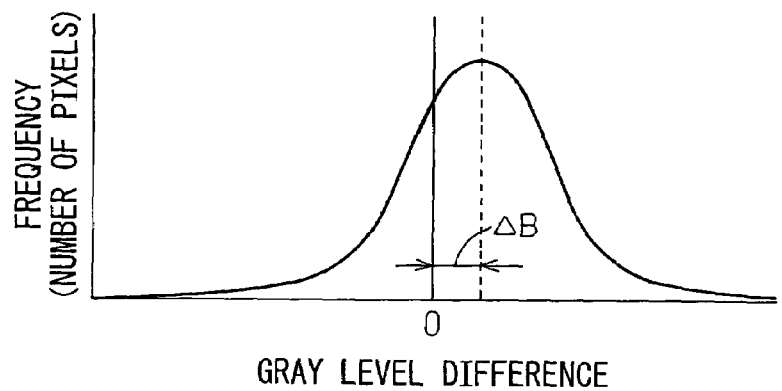
FIGS. 7A to 7C are diagrams for explaining a method of computing brightness difference.

In a specific example, the brightness difference computing section 9 computes the distribution (histogram) of the signed gray level difference supplied from the difference detection section 6, and computes the brightness difference by obtaining the value ΔB corresponding to the gray level difference at which the distribution peaks, as shown in FIG. 7A.

Figure 7B:
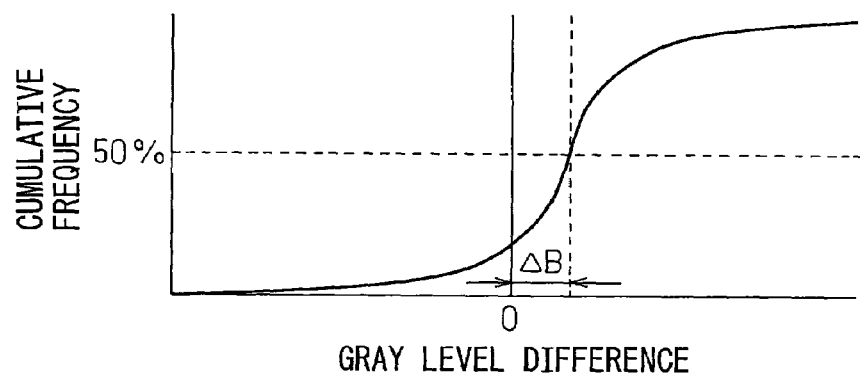

Alternatively, as shown in FIG. 7B, the brightness difference computing section 9 computes the brightness difference by obtaining the value ΔB corresponding to the gray level difference having a prescribed frequency value (for example, 50%) in the gray level difference cumulative frequency output from the cumulative frequency computing section 21.

Figure 7C:
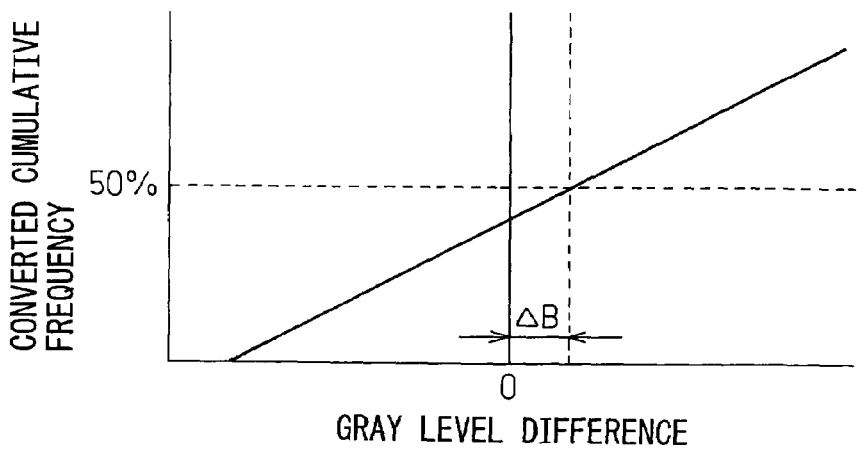

Further alternatively, as shown in FIG. 7C, the brightness difference computing section 9 computes the brightness difference by obtaining the value ΔB corresponding to the gray level difference having a prescribed frequency value (for example, 50%) in the approximate straight line output from the approximate straight line computing section 23. Since this method uses the approximate straight line, the calculation of the brightness difference is easy.

Figure 8:
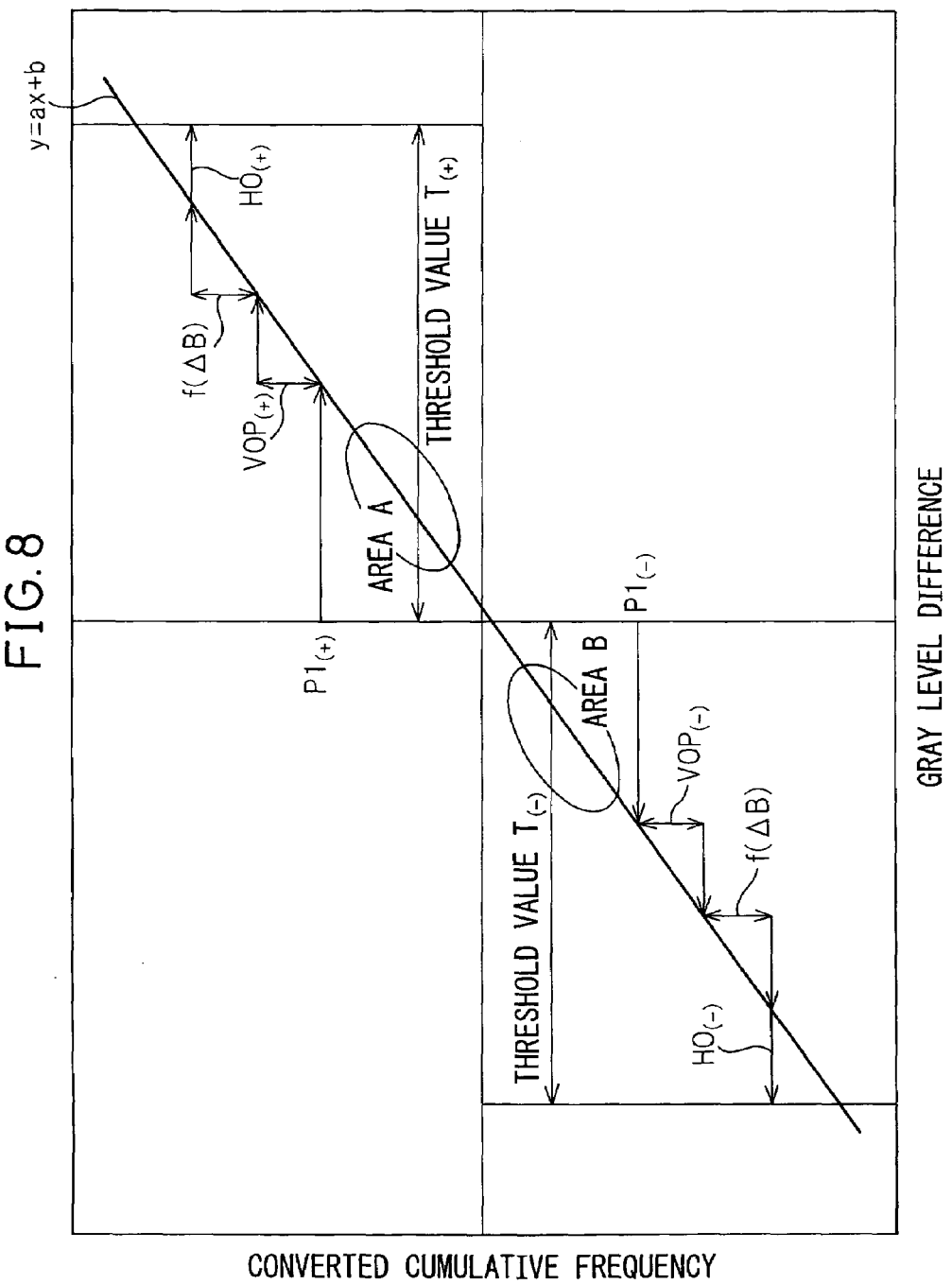
FIG. 8 is a diagram for explaining a first example of the process for determining the threshold value using the converted cumulative frequency of the signed gray level difference.

In step S107, the threshold value determining section 24 determines the detection threshold values $T_{(+)}$ and $T_{(-)}$ by applying the slope (a) and intercept (b), i.e., the parameters, of the approximate straight line, the brightness difference (ΔB) computed by the brightness difference computing section 9, and the prescribed cumulative frequency values $P1_{(+)}$ and $P1_{(-)}$ to the following prescribed equations (see FIG. 8).

$$T_{(+)} = a(P1_{(+)} + VO_{(+)} + f(\Delta B)) + b + HO_{(+)}$$

$$T_{(-)} = a(P1_{(-)} + VO_{(-)} - f(\Delta B)) + b - HO_{(-)}$$

Here, $P1_{(+)}$ and $P1_{(-)}$ are cumulative frequencies corresponding to the cumulative probabilities (p) and (−p), respectively, $VOP_{(+)}$, $HO_{(+)}$, $VOP_{(-)}$, and $HO_{(-)}$ are fixed sensitivity setting parameters, and f(ΔB) is an arbitrary function for correcting the threshold value in accordance with the brightness difference ΔB. $f(\Delta B) = \alpha |\Delta B|$ (where α is a fixed coefficient) can be given an example of f(ΔB).

After the positive threshold value $T_{(+)}$ and the negative threshold value $T_{(-)}$ have been determined, the detection section 8 determines whether there exist any defects in the captured image pattern of the die by checking whether the gray level difference ΔGL of each pixel lies within the range defined by the thus determined threshold values $T_{(+)}$ and $T_{(-)}$.

Figure 9:
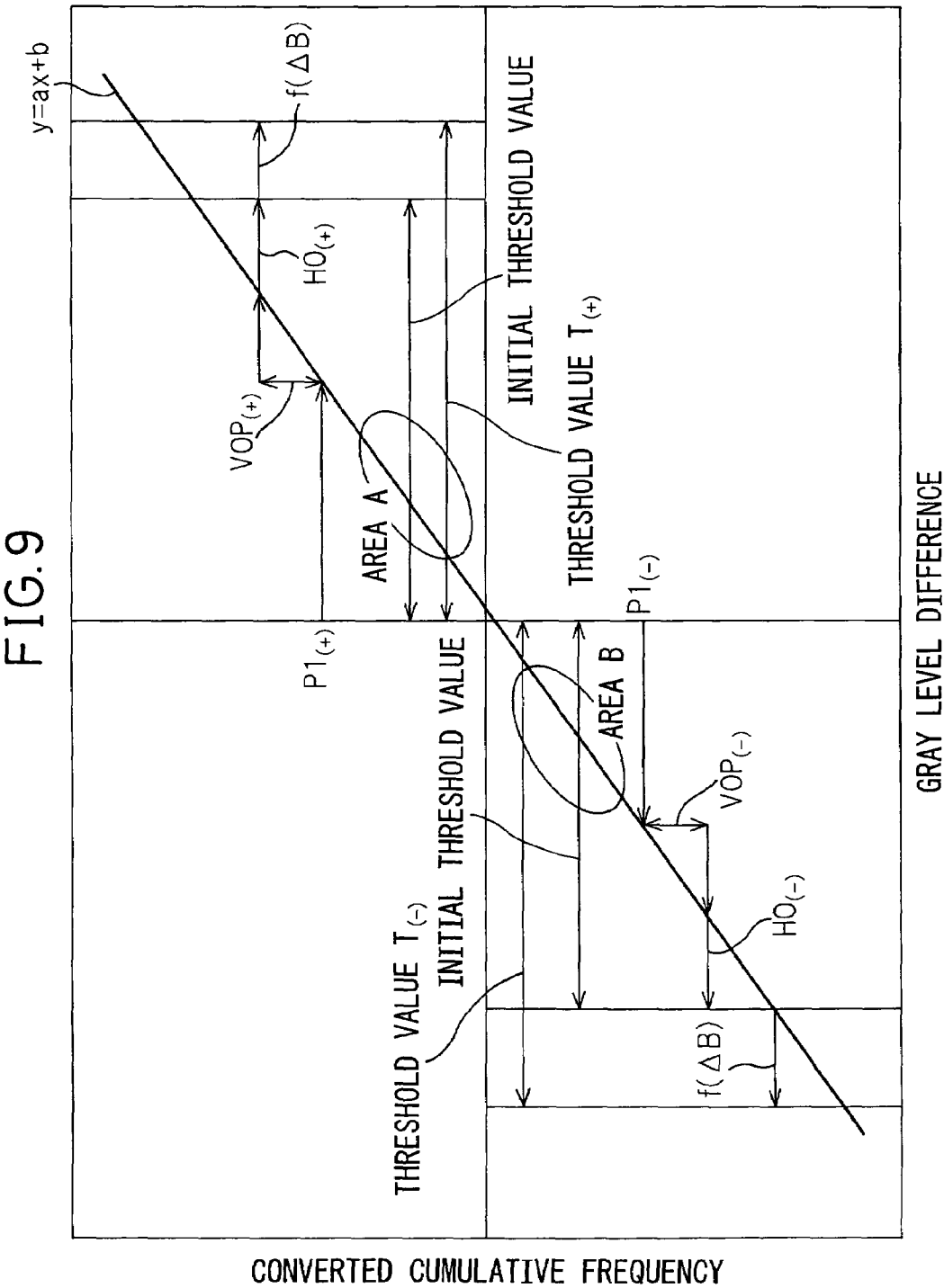
FIG. 9 is a diagram for explaining a second example of the process for determining the threshold value using the converted cumulative frequency of the signed gray level difference.

Alternatively, if the detection threshold values are given by some other means, the threshold values may be corrected more simply by the following equations (see FIG. 9).

$$T_{(+)} = \text{Initial threshold value on the positive side} + f(\Delta B)$$

$$T_{(-)} = \text{Initial threshold value on the negative side} - f(\Delta B)$$

When a monotonically increasing function such as $f(\Delta B) = \alpha |\Delta B|$ is used as f(ΔB) for the brightness difference as described above, the positive threshold value $T_{(+)}$ increases with the brightness difference (ΔB), and the negative threshold value $T_{(-)}$ decreases with the brightness difference (ΔB). In this way, the threshold value range ($T_{(-)}$ to $T_{(+)}$) expands as the brightness difference between the images of the dies under comparison, that is, color unevenness, increases; accordingly, the occurrence of false defects is reduced by expanding the threshold value range in accordance with the spreading of the distribution of the gray level difference associated with color unevenness.

Figure 10:
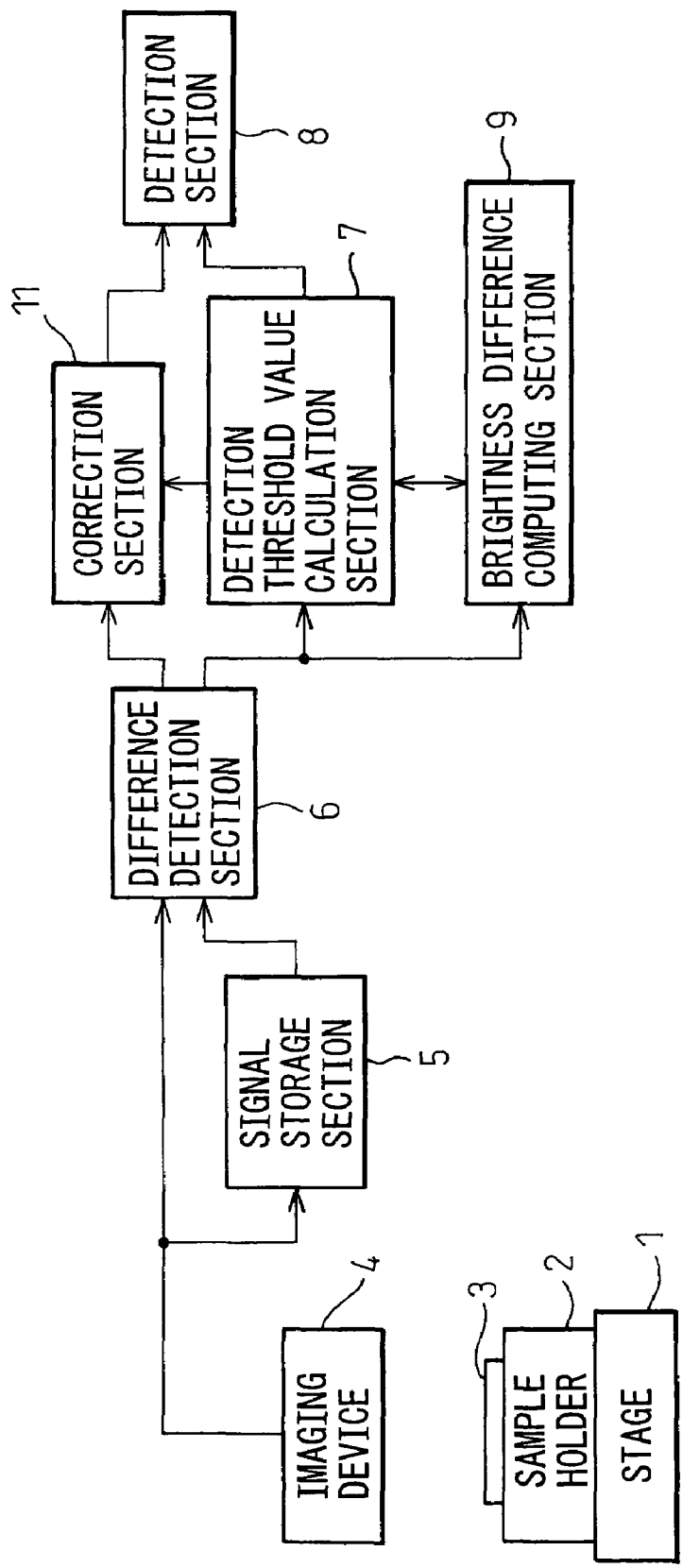
FIG. 10 is a block diagram showing the general configuration of an appearance inspection apparatus according to a second embodiment of the present invention.

FIG. 10 is a block diagram showing the general configuration of an appearance inspection apparatus according to a second embodiment of the present invention. The appearance inspection apparatus of the second embodiment is similar in configuration to that of the first embodiment, but differs by the inclusion of a correction section 11 which corrects a signed gray level difference signal containing color unevenness to a corrected absolute gray level difference signal.

The difference detection section 6 detects the positive- or negative-signed gray level difference, as in the first embodiment, and supplies the signed gray level difference to the detection threshold value calculation section 7 and the correction section 11. The detection threshold value calculation section 7 determines positive and negative two threshold values T(+) and T(−) from the signed gray level difference, and supplies (T(+)−T(−))/2 as the threshold value to the detection section 8. The detection threshold value calculation section 7 calculates the average value (T(+)+T(−))/2 of the positive and negative threshold values T(+) and T(−), and supplies it as the correction value to the correction section 11. The correction section 11 calculates a signed corrected gray level difference by subtracting the correction value from the signed gray level difference, and converts it into an absolute value which is supplied to the detection section 8. The detection section 8 judges the unsigned corrected absolute gray level difference by using (T(+)−T(−))/2 as the threshold value.

Determining the two, positive and negative, threshold values and calculating from them the threshold value and the corrected absolute gray level difference for comparison, as in the second embodiment, is effective not only in the case where, as in the second embodiment, the detection threshold value calculation section 7 does not determine the threshold value by computing the converted cumulative frequency and then computing the approximate straight line, but also in the case where the threshold value is determined by some other method, for example, where the threshold value is determined without inversely converting from the histogram.

Figure 11:
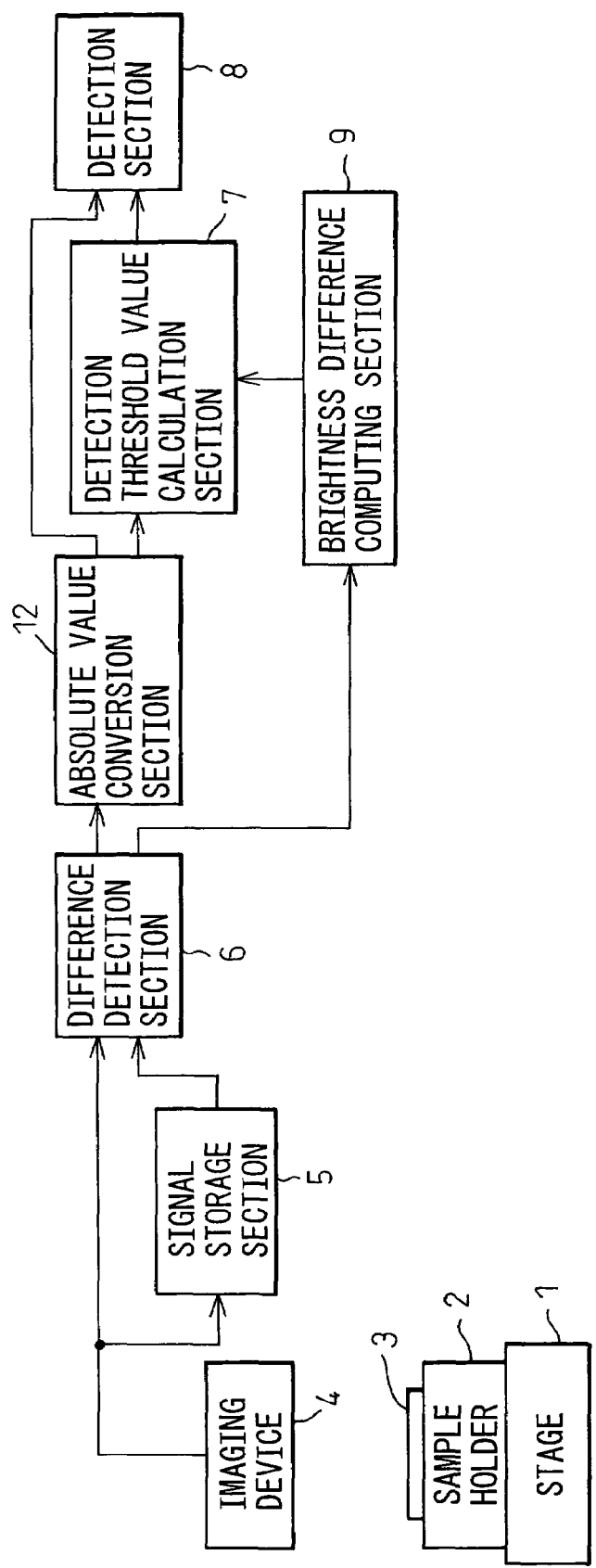
FIG. 11 is a block diagram showing the general configuration of an appearance inspection apparatus according to a third embodiment of the present invention.
Figure 12C:
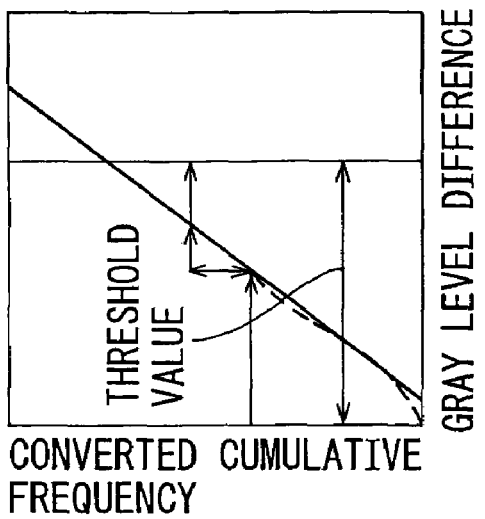
FIGS. 12A to 12C are diagrams for explaining a method of computing the converted cumulative frequency of an absolute gray level difference.
Figure 12B:
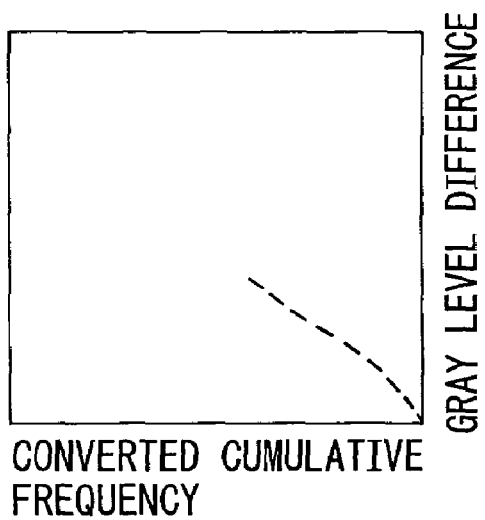
Figure 12A:
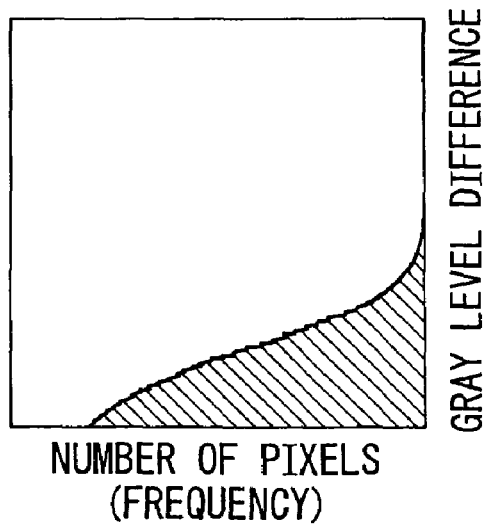

FIG. 11 is a block diagram showing the general configuration of an appearance inspection apparatus according to a third embodiment of the present invention. In the appearance inspection apparatus of the third embodiment, the signed gray level difference signal detected by the difference detection section 6 is converted by an absolute value conversion section 12 into an unsigned absolute gray level difference signal; then, based on the absolute gray level difference signal, the detection threshold value calculation section 7 determines an absolute threshold value, and the detection section 8 performs a defect inspection by comparing the absolute gray level difference signal with the absolute threshold value.

Here, the detection threshold value calculation section 7 determines the absolute threshold value based on the absolute gray level difference signal, in a manner similar to the above-described method in which the positive and negative two threshold values were determined from the singed gray level difference signal.

More specifically, in step S101, the signed gray level difference calculated pixel by pixel by the difference detection section 6 is first converted into the absolute gray level difference by the absolute value conversion section 12, and then input to the cumulative frequency computing section 21.

In step S102, the cumulative frequency computing section 21 creates a histogram of gray level differences such as shown in 12A. Here, as in the first embodiment, the histogram may be created by using the gray level differences only of selectively sampled pixels.

In step S103, the cumulative frequency computing section 21 creates the cumulative frequency of the gray level difference based on the histogram. Here, instead of the cumulative frequency, cumulative probability may be created. The cumulative frequency computing section 21 supplies the thus created cumulative frequency to the conversion section 22.

In step S104, assuming that the gray level difference obeys a certain type of distribution such as a normal distribution, a Poisson distribution, or a chi-squared distribution, the conversion section 22 converts the cumulative frequency so that the cumulative frequency shows a linear relationship to the gray level difference in the assumed distribution.

Figure 13A:
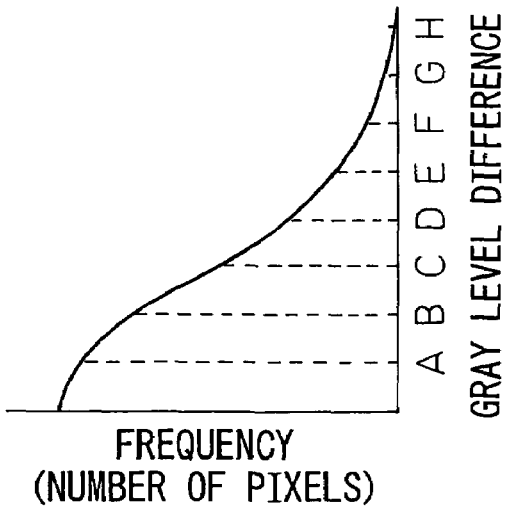
FIGS. 13A to 13C are diagrams for explaining the process for computing the converted cumulative frequency of the absolute gray level difference.
Figure 13B:
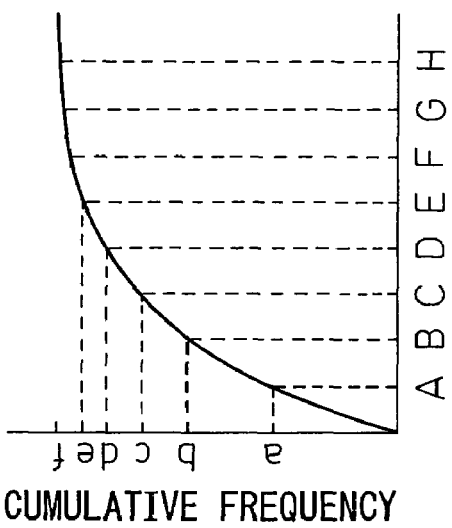
Figure 13C:
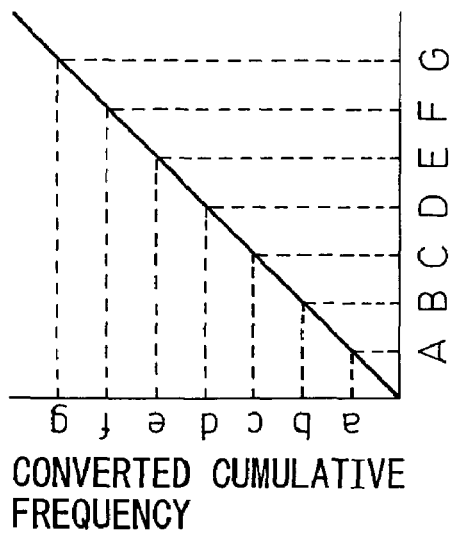

It is assumed that the frequency of the gray level difference has a certain distribution such as shown in FIG. 13A. Then, its cumulative frequency is a monotonically increasing curve such as shown in FIG. 13B. If the curve is represented by probabilities by dividing each cumulative frequency by the total number of samples, curves having the same coefficient, which shows how widespread the distribution is, are identical. Next, the cumulative frequency is converted so that the cumulative frequency shows a linear relationship to the gray level difference. To describe more specifically, if values "a" to "f" (actually, "a" to "h", though not shown) in FIG. 13B are converted so that they are proportional to values A to F (A to H), the graph shown in FIG. 13C results; here, if the values A to G (A to H) are equally spaced apart, then the values "a" to "g" ("a" to "h") are also equally spaced apart. To describe this process more specifically, the conversion is accomplished by converting the cumulative probability by using the inverse function $F^{-1}(t)$ of the cumulative probability $F(t)$ (cumulative frequency/number of samples) where the probability of the gray level difference is denoted by $f(t)$. The converted cumulative frequency thus obtained is represented by a graph close to a straight line, such as shown in FIG. 13C. In the figure, the graph is shown in terms of cumulative frequency, but the graph is the same if it is shown in terms of cumulative probability. The converted cumulative frequency thus obtained is supplied to the approximate straight line computing section 23 at the subsequent stage.

Here, instead of performing the calculation for obtaining the inverse function of the cumulative probability, a conversion table may be constructed in advance in accordance with the distribution, as in the first embodiment, and the conversion may be performed using the conversion table. Further, the conversion need only be performed on the points necessary to obtain the approximate straight line hereinafter described.

The assumed distribution can be created in advance by using a reference sample or a portion of the sample, as in the first embodiment. As for the method of creating the assumed distribution from the reference, a histogram of gray level differences is created covering a region sufficiently larger than the range used to obtain the threshold value in the inspection. At this time, dies free from imperfections such as color unevenness or an area containing such dies is selected, or the average value of the signed gray level differences is obtained and a correction is made so that the gray level difference becomes zero at the average value, or a correction is made so that the gray level difference becomes zero when the probability is 50%. Then, the conversion table is constructed by obtaining the cumulative probability for each of the equally spaced gray level differences.

In step S105, the approximate straight line computing section 23 computes the approximate straight line (y=ax+b) from the relationship between the gray level difference and the converted cumulative frequency, and supplies it to the threshold value determining section 25.

In step S106, in the same manner as in the first embodiment, the brightness difference computing section 9 computes the brightness difference between the two images under comparison, based on the signed gray level difference signal, the cumulative frequency of the signed gray level difference, or the approximate straight line of the converted cumulative frequency based thereon.

Figure 14A:
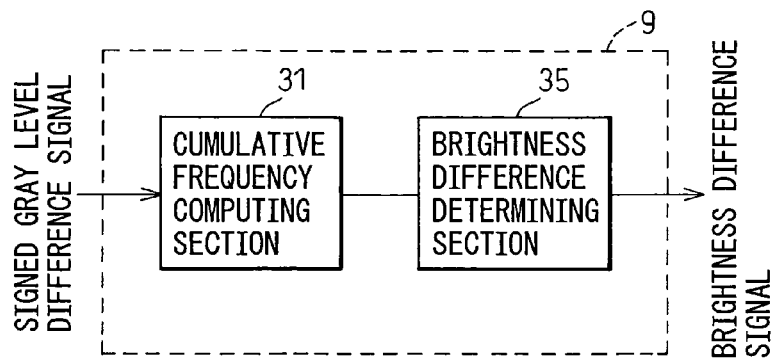
FIGS. 14A to 14C are diagrams showing the general configuration of a brightness difference computing section in the appearance inspection apparatus of FIG. 11.
Figure 14B:
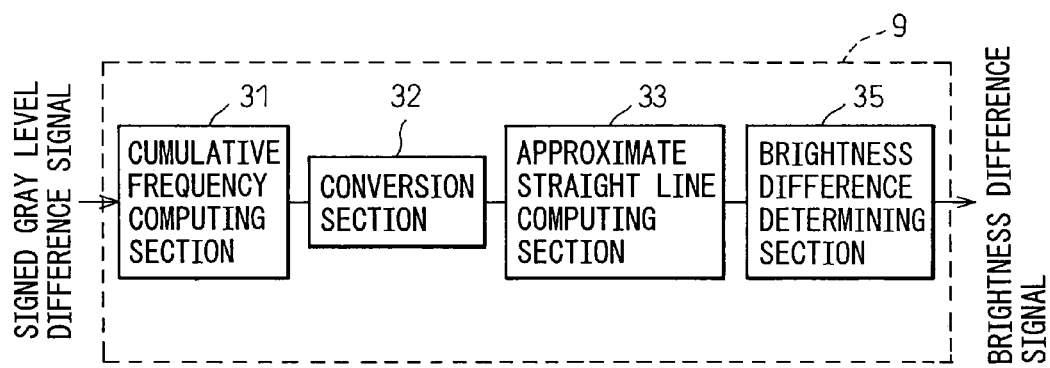
Figure 14C:
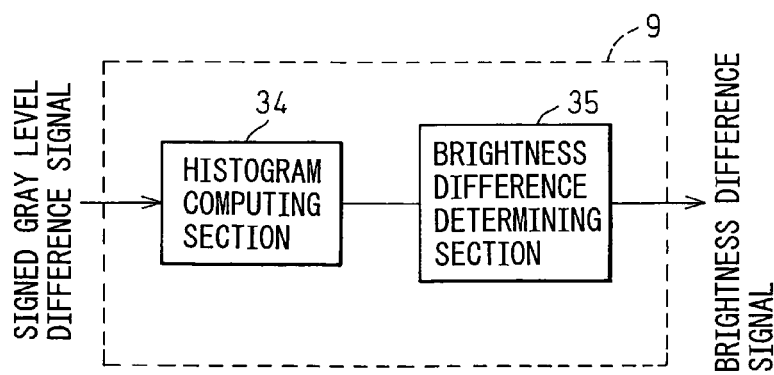

For this purpose, the brightness difference computing section 9 comprises, as shown in FIGS. 14A to 14C, a cumulative frequency computing section 31 for computing the cumulative frequency based on the signed gray level difference signal, a conversion section 32 for converting the cumulative frequency of the signed gray level difference into the converted cumulative frequency, and an approximate straight line computing section 33 for computing the approximate straight line of the converted cumulative frequency, separately from the cumulative frequency computing section 21, the conversion section 22, and the approximate straight line computing section 23 provided in the detection threshold value calculation section 7. In operation, the above sections are the same as the cumulative frequency computing section 21, the conversion section 22, and the approximate straight line computing section 23 provided in the detection threshold value calculation section 7 in the first embodiment, and therefore, a description thereof will not be given here.

When computing the brightness difference, for example, in relation to the gray level difference having a prescribed frequency in the cumulative frequency of the signed gray level difference, the brightness difference computing section 9 comprises, as shown in FIG. 14A, the cumulative frequency computing section 31 and a brightness difference determining section 35 for determining the brightness difference based on the cumulative frequency.

Further, when computing the brightness difference, for example, in relation to the gray level difference having a prescribed frequency in the approximate straight line, the brightness difference computing section 9 comprises, as shown in FIG. 14B, the cumulative frequency computing section 31, the conversion section 32, the approximate straight line computing section 33, and the brightness difference determining section 35 for determining the brightness difference based on the approximate straight line.

On the other hand, when computing the brightness difference, for example, in relation to the gray level difference corresponding to the peak of the distribution of the signed gray level difference, the brightness difference computing section 9 comprises a histogram computing section 34 for computing the histogram of the signed gray level difference and the brightness difference determining section 35 for determining the brightness difference based on the histogram.

The brightness difference signal output from the brightness difference determining section 35 is supplied to the threshold value determining section 24 in the detection threshold value calculation section 7.

Figure 15A:
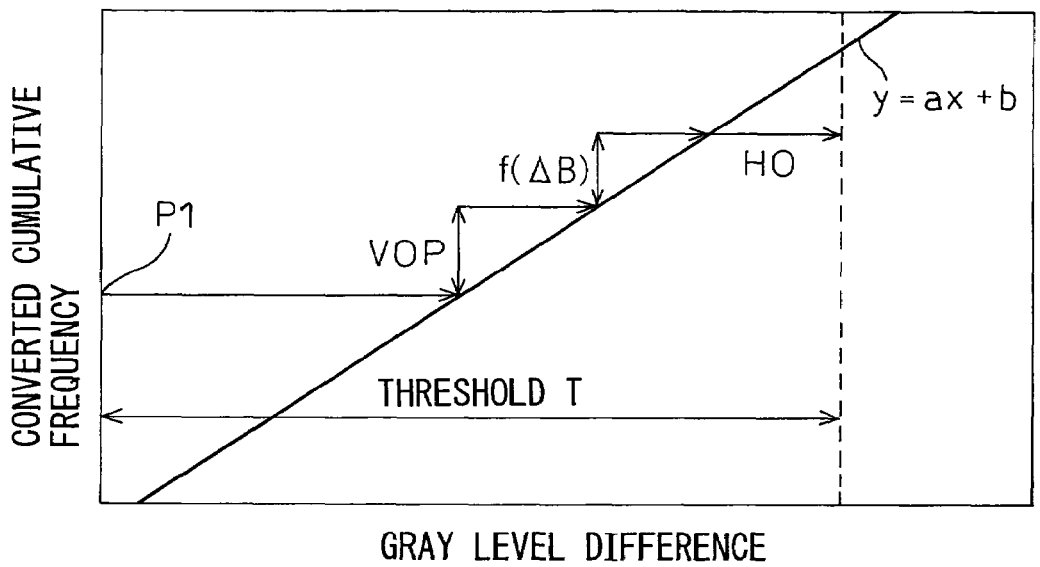
FIGS. 15A and 15B are diagrams for explaining the process for determining the threshold value using the converted cumulative frequency of the absolute gray level difference.

In step S107, the threshold value determining section 24 determines the detection threshold value T by applying the slope (a) and intercept (b), i.e., the parameters, of the approximate straight line, the brightness difference ($\Delta B$) computed by the brightness difference computing section 9, and the prescribed cumulative frequency value P1 to the following prescribed equation (see FIG. 15A).

$$T=a(P1+VO+f(\Delta B))+b+HO$$

Here, P1 is the cumulative frequency corresponding to the cumulative probability (p), VOP and HO are fixed sensitivity setting parameters, and $f(\Delta B)$ is an arbitrary function for correcting the threshold value in accordance with the brightness difference $\Delta B$. A monotonically increasing function such as f(ΔB)=α|ΔB| (where α is a fixed coefficient), for example, may be used as f(ΔB) for the brightness difference.

After the threshold value T has been determined, the detection section 8 determines whether there exists any defect in the captured image pattern of the die by checking whether the gray level difference ΔGL of each pixel exceeds the thus determined threshold value T.

Figure 15B:
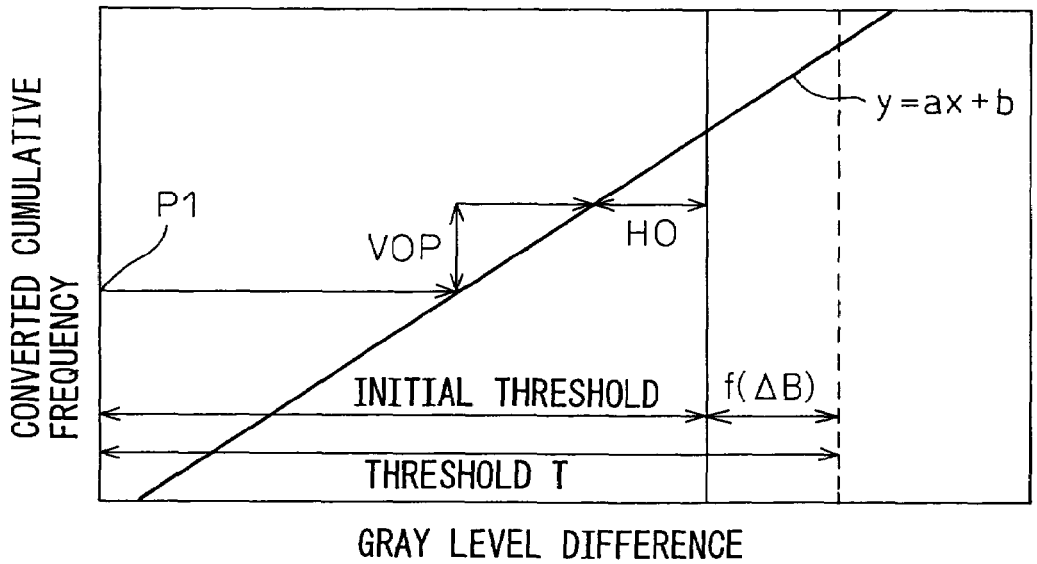

Alternatively, if the detection threshold value is given by some other means, the threshold value may be corrected more simply by the following equation (see FIG. 15B).

$$T = \text{Initial threshold value} + f(\Delta B)$$

When a monotonically increasing function is used as f(ΔB) for the brightness difference as described above, the detection threshold value T increases with the brightness difference (ΔB). Accordingly, the occurrence of false defects is reduced by expanding the threshold value range in accordance with the spreading of the distribution of the gray level difference associated with color unevenness.

Figure 16:
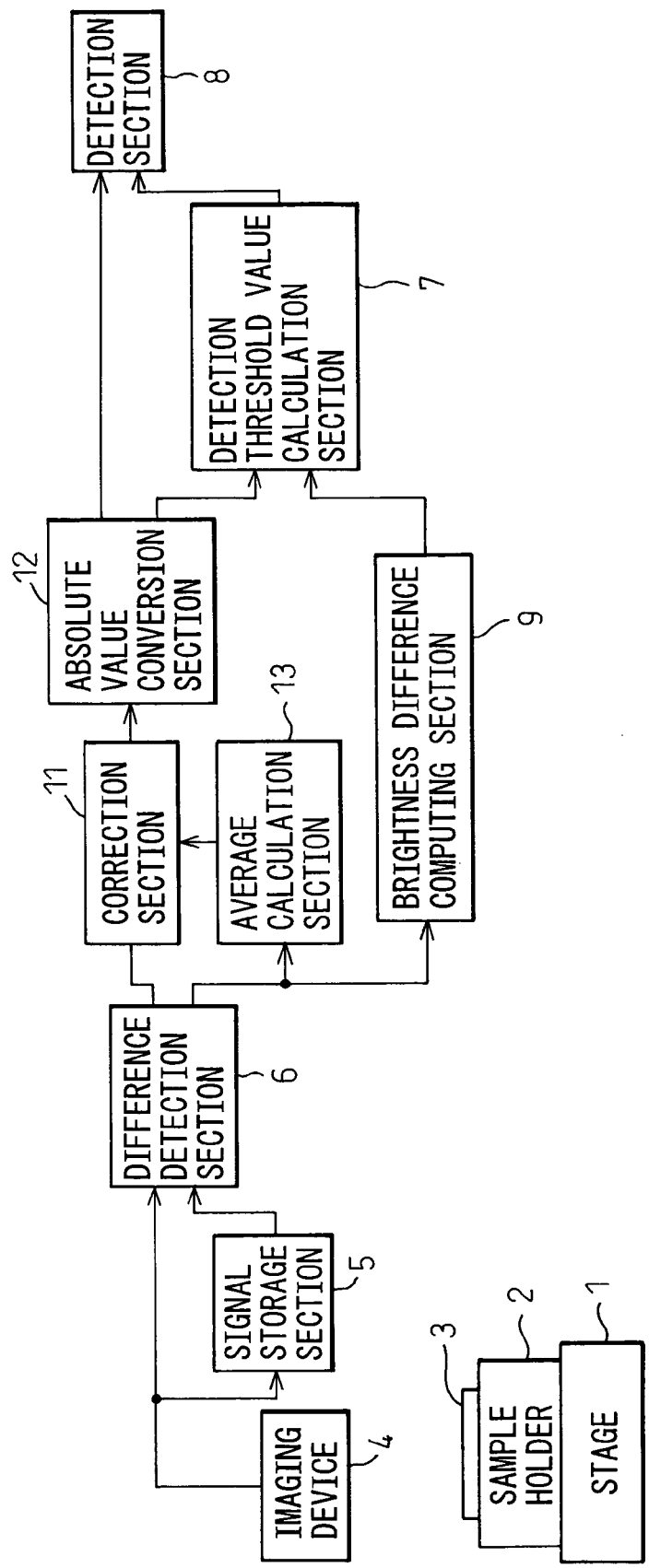
FIG. 16 is a block diagram showing the general configuration of an appearance inspection apparatus according to a fourth embodiment of the present invention.

FIG. 16 is a block diagram showing the general configuration of an appearance inspection apparatus according to a fourth embodiment of the present invention.

Here, the difference detection section 6 detects the positive- or negative-signed gray level difference, and supplies it to an average calculation section 13 as well as to the correction section 11 and the brightness difference computing section 9.

The average calculation section 13 calculates the average of the positive- or negative-signed gray level differences of all the pixels or of selectively sampled pixels. If the centers of the distributions of the gray levels of two images coincide with each other, the average of the gray level differences should become zero, and any deviation of the calculated average from zero indicates the displacement between the two distributions.

The correction section 11 computes a signed corrected gray level difference by correcting the positive- or negative-signed gray level difference by an amount equal to the deviation from zero of the average of the positive- or negative-signed differences calculated by the average calculation section 13. The signed corrected gray level differences thus computed have a distribution centered on zero. The absolute value conversion section 12 converts the signed corrected gray level difference into an unsigned corrected absolute gray level difference which is supplied to the detection threshold value calculation section 7 and the detection section 8. The processing performed in the detection threshold value calculation section 7, the detection section 8, and the brightness difference computing section 9 is the same as that performed in the third embodiment.

Here, rather than making the correction by obtaining the average of the signed gray level differences, the gray level differences at which the cumulative frequencies in the two distributions are 50% may be obtained, and a correction may be made so that they coincide with each other.

By computing the signed corrected gray level differences and the corrected absolute gray level differences and using them for subsequent processing, as in the fourth embodiment, the displacement between the distributions of the two images can be corrected, and errors caused by the displacement in distribution can be reduced.

According to the present invention, if there is a brightness difference (color unevenness) between the two images under comparison, the detection threshold value is automatically set larger in accordance with the brightness difference; as a result, if the distribution of the gray level differences spreads due to color unevenness, the occurrence of false defects can be reduced. Further, according to the present invention, as much of the processing required to detect the brightness difference can be performed as a part of the threshold value setting process, the setting of the threshold value that matches the brightness difference can be accomplished in a very short time.

Furthermore, when the above-described image defect inspection method or apparatus is applied to an appearance inspection apparatus for detecting a defect in a semiconductor circuit pattern formed on a semiconductor wafer, a high-throughput semiconductor pattern appearance inspection apparatus capable of automatically setting the threshold value in accordance with the noise level of the pattern can be achieved.

The present invention is applicable to an image defect inspection method and apparatus in which two corresponding images under inspection are compared and, if the difference is large, either one of them is judged to be defective; in particular, the invention is applicable to an appearance inspection apparatus for detecting a defect in a circuit pattern such as a semiconductor circuit pattern formed on a semiconductor wafer.

While the invention has been described with reference to specific embodiments chosen for purpose of illustration, it should be apparent that numerous modifications could be made thereto by those skilled in the art without departing from the basic concept and scope of the invention.

What is claimed is:

1. An image defect inspection method comprising:
   detecting a gray level difference between corresponding portions of two images;
   changing a threshold value in accordance with the distribution of said detected gray level difference;
   comparing said detected gray level difference with said threshold value;
   judging one of said corresponding portions to be defective if said gray level difference is larger than said threshold value;
   computing a brightness difference between said two images, wherein said threshold value is determined in such a manner that said threshold value increases with said computed brightness difference;
   detecting a positive- or negative-signed gray level difference between the corresponding portions of said two images;
   computing a cumulative frequency of said detected signed gray level difference;
   computing a converted cumulative frequency by converting said cumulative frequency so that said cumulative frequency shows a linear relationship to said signed gray level difference when said signed gray level difference is assumed to have a distribution that obeys a prescribed type of distribution;
   computing an approximate straight line by approximating said converted cumulative frequency by a straight line; and
   computing said brightness difference in relation to a signed gray level difference having a prescribed frequency in said approximate straight line.

2. An image defect inspection method comprising:
   detecting a gray level difference between corresponding portions of two images;
   changing a threshold value in accordance with the distribution of said detected gray level difference;
   comparing said detected gray level difference with said threshold value;

judging one of said corresponding portions to be defective if said gray level difference is larger than said threshold value;

computing a brightness difference between said two images, wherein said threshold value is determined in such a manner that said threshold value increases with said computed brightness difference;

detecting a positive- or a negative-signed gray level difference between the corresponding portions of said two images, computing an unsigned absolute gray level difference from said positive- or a negative-signed gray level difference;

computing a cumulative frequency of said absolute gray level difference;

computing a converted cumulative frequency by converting said cumulative frequency so that said cumulative frequency shows a linear relationship to said absolute gray level difference when said absolute gray level difference is assumed to have a distribution that obeys a prescribed type of distribution;

computing an approximate straight line by approximating said converted cumulative frequency by a straight line;

determining an absolute threshold value by applying said approximate straight line, a prescribed cumulative frequency value, and said brightness difference to a prescribed calculation method; and performing said comparison using said absolute gray level difference and said absolute threshold value.

3. An image defect inspection method comprising:

detecting a gray level difference between corresponding portions of two images;

changing a threshold value in accordance with the distribution of said detected gray level difference;

comparing said detected gray level difference with said threshold value;

detecting a positive- or a negative-signed gray level difference between the corresponding portions of said two images;

computing a center of distribution of the positive- or a negative-signed gray level difference from zero, as a brightness difference between the two images;

determining said threshold value according to said computed brightness difference in such a manner that said threshold value increases with said computed brightness difference; and determining one of said corresponding portions to be defective if said gray level difference is larger than said threshold value wherein a cumulative frequency of said signed gray level difference is computed, a converted cumulative frequency is computed by converting said cumulative frequency so that said cumulative frequency shows a linear relationship to said signed gray level difference when said signed gray level difference is assumed to have a distribution that obeys a prescribed type of distribution, an approximate straight line is computed by approximating said converted cumulative frequency by a straight line, and two positive and negative threshold values are determined by applying said approximate straight line, a prescribed cumulative frequency value, and said brightness difference to a prescribed calculation method.

4. An image defect inspection method as claimed in claim 3, wherein said brightness difference is computed in relation to said signed gray level difference having a prescribed frequency in said computed cumulative frequency of said signed gray level difference.

5. An image defect inspection method as claimed in claim 3, wherein said brightness difference is computed in relation to said signed gray level difference having a prescribed frequency in said approximate straight line.

6. An image defect inspection method as claimed in claim 3, wherein said brightness difference is computed in relation to a gray level difference at which the distribution of said detected signed gray level difference peaks.

7. An image defect inspection apparatus comprising:

a difference image detection section which detects a gray level difference between the corresponding portions of two images;

a defect detection section which compares said detected gray level difference with a threshold value, and judges one of said portions to be defective if said gray level difference is larger than said threshold value;

a detection threshold value calculation section which changes said threshold value in accordance with the distribution of said detected gray level difference; and a brightness difference computing section which computes a brightness difference between said two images, wherein said detection threshold value calculation section determines said threshold value in such a manner that said threshold value increases with said computed brightness difference, wherein said difference image detection section detects a positive- or negative-signed gray level difference, and wherein said detection threshold value calculation section comprises:

a cumulative frequency computing section which computes a cumulative frequency of said signed gray level difference;

a conversion section which computes a converted cumulative frequency by converting said cumulative frequency so that said cumulative frequency shows a linear relationship to said signed gray level difference when said signed gray level difference is assumed to have a distribution that obeys a prescribed type of distribution;

an approximate straight line computing section which computes an approximate straight line by approximating said converted cumulative frequency by a straight line; and a threshold value determining section which determines two, positive and negative, threshold values by applying said approximate straight line, a prescribed cumulative frequency value, and said brightness difference to a prescribed calculation method.

8. An image defect inspection apparatus as claimed in claim 7, wherein said brightness difference computing section computes said brightness difference in relation to said signed gray level difference having a prescribed frequency in said computed cumulative frequency of said signed gray level difference.

9. An image defect inspection apparatus as claimed in claim 7, wherein said brightness difference computing section computes said brightness difference in relation to said signed gray level difference having a prescribed frequency in said approximate straight line.

10. An image defect inspection apparatus as claimed in claim 7, wherein said brightness difference computing section computes said brightness difference in relation to a gray level difference at which the distribution of said detected signed gray level difference peaks.

* * * * *